US009802035B2

(12) United States Patent
Masterson et al.

(10) Patent No.: US 9,802,035 B2
(45) Date of Patent: Oct. 31, 2017

(54) APPARATUS FOR ELECTRICALLY MEDIATED DELIVERY OF THERAPEUTIC AGENTS

(71) Applicant: Ichor Medical Systems, Inc., San Diego, CA (US)

(72) Inventors: Steven P. Masterson, Encinitas, CA (US); Andrew W. Hannaman, San Diego, CA (US); Robert M. Bernard, Las Vegas, NV (US)

(73) Assignee: ICHOR MEDICAL SYSTEMS, INC., San Diego, CA (US)

( * ) Notice: Subject to any disclaimer, the term of this patent is extended or adjusted under 35 U.S.C. 154(b) by 0 days.

(21) Appl. No.: 15/153,558

(22) Filed: May 12, 2016

(65) Prior Publication Data

US 2017/0050015 A1 Feb. 23, 2017

Related U.S. Application Data

(63) Continuation of application No. 10/591,806, filed as application No. PCT/US2005/007936 on Mar. 8, 2005, now Pat. No. 9,364,664.
(Continued)

(51) Int. Cl.
*A61N 1/05* (2006.01)
*A61N 1/32* (2006.01)
(Continued)

(52) U.S. Cl.
CPC ............ *A61N 1/0502* (2013.01); *A61N 1/325* (2013.01); *A61N 1/327* (2013.01); *A61N 1/08* (2013.01); *A61N 1/30* (2013.01)

(58) Field of Classification Search
CPC ...... A61N 1/0502; A61N 1/327; A61N 1/325; A61N 1/08; A61N 1/30
See application file for complete search history.

(56) References Cited

U.S. PATENT DOCUMENTS 2,725,877 A 12/1955 Reiter et al.
2,860,439 A 11/1958 Johnson
(Continued)

FOREIGN PATENT DOCUMENTS

CN 1312728 A 9/2001
CN 1345607 A 4/2002
(Continued)

OTHER PUBLICATIONS

AU550342 Examination Report dated Mar. 5, 2009.
(Continued)

*Primary Examiner* — Mark W Bockelman
(74) *Attorney, Agent, or Firm* — Wilson Sonsini Goodrich & Rosati

(57) ABSTRACT

Apparatus for the delivery of an electrical field which facilitates the intracellular delivery of a therapeutic agent to a predetermined site within the tissue of a patient. The apparatus will comprise a plurality of penetrating electrodes arranged in a predetermined spatial relationship, each electrode with a cross sectional area contributing to the total cross sectional area of all electrodes, and structural means incorporating an inanimate source of energy operatively connected to the plurality of electrodes for deploying the electrodes, wherein the source of energy is sufficient to impart a force of at least 1000 pounds per square inch (0.7 kilogram per square millimeter) of total cross sectional area of all electrodes at the initiation of the deployment of the electrodes. The apparatus will also comprise means for generating an electrical field which facilitates the intracellular delivery of a therapeutic agent, which means is operatively connected to said electrodes at least in their deployed state.

21 Claims, 5 Drawing Sheets

Related U.S. Application Data

(60) Provisional application No. 60/551,679, filed on Mar. 8, 2004.

(51) Int. Cl.
*A61N 1/08* (2006.01)
*A61N 1/30* (2006.01)

(56) References Cited

U.S. PATENT DOCUMENTS

| | | |
|---|---|---|
| 4,108,177 A | 8/1978 | Pistor |
| 4,198,975 A | 4/1980 | Haller |
| 4,394,863 A | 7/1983 | Bartner |
| 4,636,197 A | 1/1987 | Chu |
| 4,832,682 A | 5/1989 | Sarnoff |
| 5,141,496 A | 8/1992 | Dalto et al. |
| 5,215,089 A | 6/1993 | Baker, Jr. |
| 5,273,525 A | 12/1993 | Hofmann |
| 5,306,236 A | 4/1994 | Blumenfeld et al. |
| 5,318,514 A | 6/1994 | Hofmann |
| 5,383,851 A | 1/1995 | McKinnon, Jr. et al. |
| 5,478,316 A | 12/1995 | Bitdinger et al. |
| 5,593,429 A | 1/1997 | Ruff |
| 5,688,233 A | 11/1997 | Hofmann et al. |
| 5,702,359 A | 12/1997 | Hofmann et al. |
| 5,846,225 A | 12/1998 | Rosengart et al. |
| 5,851,197 A | 12/1998 | Marano et al. |
| 5,873,849 A | 2/1999 | Bernard |
| 5,968,006 A | 10/1999 | Hofmann |
| 6,041,252 A | 3/2000 | Walker et al. |
| 6,055,453 A | 4/2000 | Hofmann et al. |
| 6,077,247 A | 6/2000 | Marshall et al. |
| 6,110,161 A | 8/2000 | Mathiesen et al. |
| 6,120,493 A | 9/2000 | Hofmann |
| 6,159,181 A | 12/2000 | Crossman et al. |
| 6,165,720 A | 12/2000 | Felgner et al. |
| 6,199,766 B1 | 3/2001 | Fox et al. |
| 6,208,893 B1 | 3/2001 | Hofmann |
| 6,241,701 B1 | 6/2001 | Hofmann |
| 6,254,573 B1 | 7/2001 | Haim et al. |
| 6,278,895 B1 | 8/2001 | Bernard |
| 6,356,783 B1 | 3/2002 | Hubbard, Jr. |
| 6,516,223 B2 | 2/2003 | Hofmann |
| 6,520,950 B1 | 2/2003 | Hofmann et al. |
| 6,558,351 B1 | 5/2003 | Steil et al. |
| 6,678,558 B1 | 1/2004 | Dimmer et al. |
| 6,748,266 B2 | 6/2004 | Bernabei |
| 6,899,699 B2 | 5/2005 | Enggaard |
| 6,912,417 B1 | 6/2005 | Bernard et al. |
| 6,918,901 B1 | 7/2005 | Theeuwes et al. |
| 8,108,040 B2 | 1/2012 | Bernard et al. |
| 8,187,249 B2 | 5/2012 | Bernard et al. |
| 9,364,664 B2 | 6/2016 | Masterson et al. |
| 2002/0078161 A1 | 6/2002 | Cheng |
| 2002/0123675 A1 | 9/2002 | Trautman et al. |
| 2003/0083641 A1 | 5/2003 | Angel et al. |
| 2003/0083645 A1 | 5/2003 | Angel et al. |
| 2005/0154434 A1 | 7/2005 | Simon et al. |
| 2007/0021712 A1 | 1/2007 | Bernard et al. |
| 2011/0288467 A1 | 11/2011 | Bernard et al. |
| 2012/0277661 A1 | 11/2012 | Bernard et al. |

FOREIGN PATENT DOCUMENTS

| | | |
|---|---|---|
| CN | 1997423 B | 10/2012 |
| CN | ZL200580014553.1 | 10/2012 |
| EP | 2929909 A1 | 10/2015 |
| IL | 177942 A | 11/2011 |
| IL | 203766 A | 4/2012 |
| IN | 260268 | 4/2014 |
| JP | S52131684 A | 11/1977 |
| JP | S61502865 A | 12/1986 |
| JP | H04244172 A | 9/1992 |
| JP | 2000316991 A | 11/2000 |
| JP | 2001520537 A | 10/2001 |
| JP | 2002507459 A | 3/2002 |
| JP | 2002511761 A | 4/2002 |
| JP | 2004041434 A | 2/2004 |
| JP | 4362767 B2 | 11/2009 |
| JP | 5221127 B2 | 6/2013 |
| JP | 5410847 B2 | 2/2014 |
| KR | 101261642 | 4/2013 |
| MX | 296504 | 2/2012 |
| MX | 310590 | 6/2013 |
| NZ | 550342 A | 6/2010 |
| NZ | 585119 A | 8/2011 |
| SG | 136133 | 3/2011 |
| WO | WO-8601120 A1 | 2/1986 |
| WO | WO-9504562 A1 | 2/1995 |
| WO | WO-9843702 A2 | 10/1998 |
| WO | WO-9948546 A1 | 9/1999 |
| WO | WO-0007453 A1 | 2/2000 |
| WO | WO-0009184 A1 | 2/2000 |
| WO | WO-0009186 A2 | 2/2000 |
| WO | WO-0113975 A2 | 3/2001 |
| WO | WO-0113977 A1 | 3/2001 |
| WO | WO-0152731 A1 | 7/2001 |
| WO | WO-0202165 A2 | 1/2002 |
| WO | WO-03086534 A1 | 10/2003 |
| WO | WO-2004004825 A2 | 1/2004 |
| WO | WO-2004014468 A1 | 2/2004 |
| WO | WO-2005087311 A1 | 9/2005 |
| WO | WO-2008086534 A1 | 7/2008 |

OTHER PUBLICATIONS

CA2559083 Office Action dated Dec. 17, 2012.
CN200580014553.1 First Office Action dated Mar. 7, 2010.
CN200580014553.1 Second Office Action dated Aug. 16, 2010.
CN201210297392.3 Second office action dated Jul. 8, 2014.
CN201210297392.3 Third office action dated Jan. 15, 2015.
CN201210297392.3 First Office Action dated Nov. 25, 2013.
Davis et al. "The mechanics of microneedles." Second Joint EMBS-BMES Conference 2002. Conference Proceedings, 24th Annual International Conference of the Engineering in Medicine and Biology Society, Annual Fall Meeting of the Biomedical Engineering Society, Houston, TX, Oct. 2002, 1:498-499.
EP05725237.1 Office Action dated Dec. 18, 2012.
EP05725237.1 Search Report dated Mar. 11, 2011.
EP15165174.2 Extended European Search Report dated Aug. 6, 2015.
IL177942 Office Action dated Aug. 2, 2009.
IL203766 Office Action dated Dec. 20, 2010.
IN2835/KOLNP/2006 Examination Report dated Jun. 11, 2013.
IN2835/KOLNP/2006 Examination Report dated Mar. 8, 2011.
JP2003-583542 Office Action dated Aug. 11, 2008.
JP2007-503001 Final Decision dated Nov. 22, 2011.
JP2007-503001 Office Action dated Feb. 1, 2011.
JP2009-140108 Office Action dated Dec. 20, 2011.
JP2009-140108 Office Action dated Jun. 25, 2013.
JP2012-066396 Office Action dated Jun. 18, 2013.
JP2013-009962 Office Action dated Feb. 4, 2014.
JP2013-009962 Office Action dated Sep. 29, 2014.
KR10-20067020757 Office Action dated Dec. 23, 2011.
KR10-2006-7020757 Office Action dated Jul. 30, 2012.
MX/a/2011/010485 Office Action dated Aug. 2, 2012.
NZ550342 Examination Report dated Mar. 5, 2009.
NZ594442 Examination Report dated Aug. 12, 2011.
NZ594442 Further Examination Report dated Jan. 11, 2013.
PCT/US03/10337 International Search Report dated Sep. 4, 2003.
PCT/US05/07936 International Search Report dated Aug. 19, 2005.
PCT/US05/07936 International Preliminary Report on Patentability dated Sep. 13, 2006.
Poland et al. "Determination of Deltoid Fat Pad Thickness: Implications for Needle Length in Adult Immunization." JAMA 277(21):1709-1711, 1977.
Schneider, et al. "Penetration Characteristics of Hypodermic Needles in Potential Skin Stimulants: Series 1." Technical Report No. UM-HSRI-78-29, Highway Safety Research Institute, Jul. 1978, p. 1-144.

(56) References Cited

OTHER PUBLICATIONS

SG200706583-2 Written Opinion dated Mar. 2, 2010.
SG201100352-2 Written Opinion dated Jun. 27, 2012.
U.S. Appl. No. 10/117,457 Final Office Action dated Oct. 20, 2004.
U.S. Appl. No. 10/117,457 Office Action dated Apr. 15, 2004.
U.S. Appl. No. 10/117,457 Office Action dated Dec. 23, 2003.
U.S. Appl. No. 10/510,399 Final Office Action dated Feb. 17, 2011.
U.S. Appl. No. 10/510,399 Office Action dated Jun. 28, 2007.
U.S. Appl. No. 10/510,399 Office Action dated Jul. 22, 2013.
U.S. Appl. No. 10/591,806 Final Office Action dated Oct. 23, 2014.
U.S. Appl. No. 10/591,806 Office Action dated Jun. 9, 2015.
U.S. Appl. No. 11/376,619 Final Office Action dated Mar. 8, 2011.
U.S. Appl. No. 11/376,619 Office Action dated Aug. 26, 2010.
U.S. Appl. No. 11/376,619 Office Action dated Sep. 12, 2011.
U.S. Appl. No. 13/114,878 Final Office Action dated Mar. 31, 2014.
U.S. Appl. No. 13/114,878 Final Office Action dated Sep. 10, 2013.
U.S. Appl. No. 13/114,878 Office Action dated Dec. 20, 2012.
U.S. Appl. No. 13/114,878 Office Action dated Jul. 6, 2015.
U.S. Appl. No. 13/114,878 Office Action dated Oct. 24, 2014.
U.S. Appl. No. 13/450,320 Office Action dated Mar. 12, 2013.
U.S. Appl. No. 13/450,320 Final Office Action dated Aug. 9, 2013.
U.S. Appl. No. 13/450,320 Final Office action dated Feb. 4, 2014.
U.S. Appl. No. 13/450,320 Office Action dated Aug. 22, 2014.
U.S. Appl. No. 13/450,320 Office Action dated Jul. 22, 2015.
U.S. Appl. No. 13/114,878 Office Action dated Mar. 24, 2016.
U.S. Appl. No. 13/450,320 Office Action dated Dec. 9, 2015.

APPARATUS FOR ELECTRICALLY MEDIATED DELIVERY OF THERAPEUTIC AGENTS

CROSS REFERENCE

This application is a continuation of U.S. patent application Ser. No. 10/591,806, filed Aug. 6, 2009, entitled "Apparatus for electrically mediated delivery of therapeutic agents", which is a U.S. 371 application of International Patent Application Serial Number PCT/US2005/007936, filed on Mar. 8, 2005, which claims benefit of U.S. Provisional Application Ser. No. 60/551,679, filed on Mar. 8, 2004, which are each explicitly incorporated herein by reference in their entirety.

TECHNICAL FIELD

The present invention is directed to an apparatus for delivery of prophylactic and therapeutic agents to patients, and more particularly, to an apparatus utilizing electrical fields to deliver such agents intracellularly in a safe, reproducible, efficacious, and cost effective manner.

BACKGROUND OF THE INVENTION

Prophylactic and therapeutic agents have long been delivered to patients using various conventional routes of administration, such as topical, oral, intravenous, parenteral, and the like. Once administered to the patient by the selected route, the delivery of the agent to the tissue of interest and its beneficial interaction with the tissue is largely dependent on its inherent physicochemical factors, but may have been facilitated by, for example, selected components of the delivery composition such as carriers, adjuvants, buffers and excipients, and the like.

More recently, the application of electrical fields has been shown to enhance the movement and uptake of macromolecules in living tissue. Application of such electrical fields in tissue relative to the administration of a prophylactic or therapeutic agent can have desirable effects on the tissue and/or the agent to be delivered. Specifically, techniques such as electroporation and iontophoresis have been utilized to enhance the delivery and/or uptake of a variety of agents in tissue. Such agents include pharmaceuticals, proteins, antibodies, and nucleic acids. Potential clinical applications of such techniques include the delivery of chemotherapeutic drugs and/or therapeutic genes in tumors, the delivery of DNA vaccines for prophylactic and therapeutic immunization, and the delivery of nucleic acid sequences encoding therapeutic proteins.

Many devices have been described for the application of electrical fields in tissue for the purpose of enhancing agent delivery. The vast majority of these have focused on a means for effective application of the electrical fields within a target region of tissue. A variety of surface and penetrating electrode systems have been developed for generating the desired electrophysiological effects.

In spite of the promise associated with electrically mediated agent delivery and the potential clinical applications of these techniques, progress has been hampered by the lack of an effective means to achieve the overall objective of efficient and reliable agent delivery using these techniques. Significant shortcomings of current systems include a complex application procedure, unwieldy device design, potential hazards for the user and patient and the inability to provide a cost effective means for administration.

Given that safe, effective, consistent, and cost effective means for the administration of therapeutic agents are highly desirable, the development of improved application systems is well warranted. Such development should include a means for minimizing operator-associated variability and ensuring the safety of the user and the patient while providing for accommodating the differences in patient characteristics likely to be encountered during widespread clinical application of electrically mediated agent delivery.

DISCLOSURE OF THE INVENTION

The present invention provides an integrated apparatus enabling Electrically Mediated Therapeutic Agent Delivery (EMTAD) to be accomplished in a safe, consistent, and cost effective manner. The present invention allows effective intramuscular, intradermal, and/or subcutaneous administration of therapeutic or prophylactic agents such as nucleic acids, drugs, antibodies, and proteins.

In one aspect, the present invention provides an apparatus for the delivery of an electrical field which facilitates the intracellular delivery of a therapeutic agent to a predetermined site within the tissue of a patient. In this aspect, the apparatus will comprise a plurality of penetrating electrodes arranged in a predetermined spatial relationship, each electrode with a cross sectional area contributing to the total cross sectional area of all electrodes, and structural means incorporating an inanimate source of energy operatively connected to the plurality of electrodes for deploying the electrodes, wherein the source of energy is sufficient to impart a force of at least 1000 pounds per square inch (0.7 kilograms per square millimeter) of total cross sectional area of all electrodes at the initiation of the deployment of the electrodes. The apparatus will also comprise means for generating an electrical field which facilitates the intracellular delivery of a therapeutic agent, which means is operatively connected to said electrodes at least in their deployed state.

Another aspect of the invention provides the apparatus with structural means configured to accept a fluid reservoir for containing a therapeutic agent, or with the fluid reservoir itself, where the reservoir is operatively connected to at least one injection orifice, and actuation means configured to transmit the therapeutic agent through the orifice to the predetermined site within the tissue of the patient.

Other aspects of the invention include such apparatus configured to accept replaceable therapeutic agent fluid reservoir subassemblies, electrode subassemblies, and a combination thereof. Also included are include means for priming the automated mechanisms incorporated in the applicator upon insertion of the cartridge, identifying the model or type of cartridge that has been inserted, and protecting the user and patient from accidental injury associated with the usage of the apparatus.

Additional aspects of the invention include such apparatus configured to improve the functionality and ergonomics of the Applicator (i.e. the user interface) in a number of ways. The inanimate source of energy can be positioned alongside the fluid reservoir, so as to reduce the overall length of the apparatus, and improve its ease of use. The deployment of the electrodes and administration of the therapeutic agent, as well as the creation of the electrical field, can be implemented with a single activation trigger. Further, safety interlocks and shields can be included to reduce the risk of accidental discharge and inadvertent contact with the electrodes and fluid orifice.

Further improvements can be included in the design of the fluid reservoir, such as the utilization of a vial, such as a glass, polycarbonate, polyethylene, etc. vial, as a means of utilizing a dry, e.g. lyophilized, therapeutic agent and a fluid supply, and allowing the separate components to be mixed just prior to use.

Yet additional improvements can be included to render the apparatus more readily adaptable to a wide range of patients, e.g. patients with widely differing body mass indices indicating a range of the thickness of patients' subcutaneous adipose layers, or the need to adjust the depth of the predetermined site in the patient. Such improvements can include, for example, a depth gauge for adjusting the depth of the penetration of the electrodes and orifice, or the use of different length and/or diameter electrodes and orifice structures, e.g. different length and gauge of syringe needles.

DETAILED DESCRIPTION OF THE INVENTION

Figure 1:
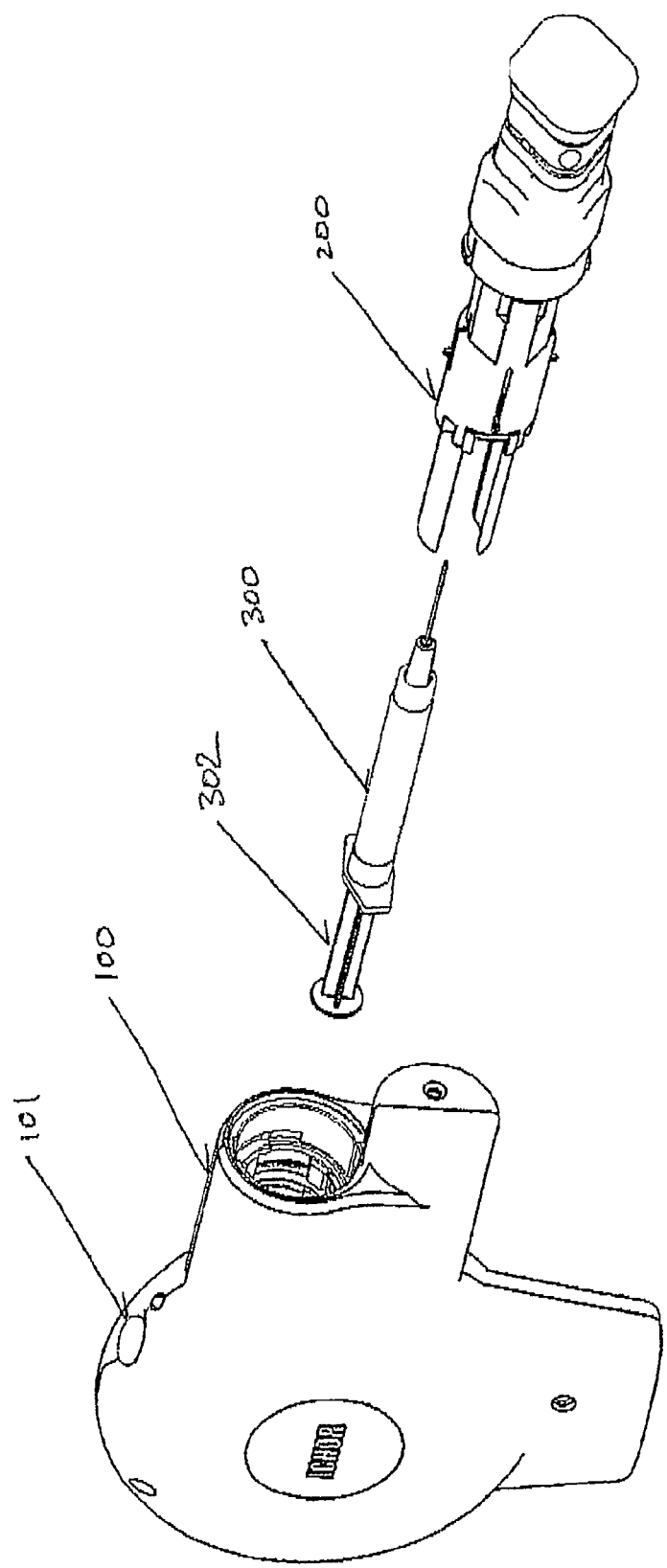
FIG. 1 illustrates three components (Applicator, Cartridge and Syringe) of an embodiment of the integrated apparatus of the present invention in an exploded view.

The present invention provides an integrated apparatus enabling Electrically Mediated Therapeutic Agent Delivery (EMTAD) to be accomplished in a safe, consistent, and cost effective manner. The present invention allows effective intramuscular, intradermal, and/or subcutaneous administration of therapeutic or prophylactic agents such as nucleic acids, drugs, antibodies, and proteins.

In one aspect, the present invention provides an apparatus for the delivery of an electrical field which facilitates the intracellular delivery of a therapeutic agent to a predetermined site within the tissue of a patient. In this aspect, the apparatus will comprise a plurality of penetrating electrodes arranged in a predetermined spatial relationship, each electrode with a cross sectional area contributing to the total cross sectional area of all electrodes, and structural means incorporating an inanimate source of energy operatively connected to the plurality of electrodes for deploying the electrodes, wherein the source of energy is sufficient to impart a force of at least 1000 pounds per square inch (0.7 kilograms per square millimeter) of total cross sectional area of all electrodes at the initiation of the deployment of the electrodes. The apparatus will also comprise means for generating an electrical field which facilitates the intracellular delivery of a therapeutic agent, which means is operatively connected to said electrodes at least in their deployed state.

Another aspect of the invention provides the apparatus with structural means configured to accept a fluid reservoir for containing a therapeutic agent, or with the fluid reservoir itself, where the reservoir is operatively connected to at least one injection orifice, and actuation means configured to transmit the therapeutic agent through the orifice to the predetermined site within the tissue of the patient.

Other aspects of the invention include such apparatus configured to accept replaceable therapeutic agent fluid reservoir subassemblies, electrode subassemblies, and a combination thereof. Also included are include means for priming the automated mechanisms incorporated in the applicator upon insertion of the cartridge, identifying the model or type of cartridge that has been inserted, and protecting the user and patient from accidental injury associated with the usage of the apparatus.

Additional aspects of the invention include such apparatus configured to improve the functionality and ergonomics of the Applicator (i.e. the user interface) in a number of ways. The inanimate source of energy can be positioned alongside the fluid reservoir, so as to reduce the overall length of the apparatus, and improve its ease of use. The deployment of the electrodes and administration of the therapeutic agent, as well as the creation of the electrical field, can be implemented with a single activation trigger. Further, safety interlocks and shields can be included to reduce the risk of accidental discharge and inadvertent contact with the electrodes and fluid orifice.

Further improvements can be included in the design of the fluid reservoir, such as the utilization of a vial, such as a glass, polycarbonate, polyethylene, etc. vial, as a means of utilizing a dry, e.g. lyophilized, therapeutic agent and a fluid supply, and allowing the separate components to be mixed just prior to use.

Yet additional improvements can be included to render the apparatus more readily adaptable to a wide range of patients, e.g. patients with widely differing body mass indices indicating a range of the thickness of patients' subcutaneous adipose layers, or the need to adjust the depth of the predetermined site in the patient. Such improvements can include, for example, a depth gauge for adjusting the depth of the penetration of the electrodes and orifice, or the use of different length and/or diameter electrodes and orifice structures, e.g. different length and gauge of syringe needles.

In general terms, the present invention will preferably provide an apparatus for the delivery of a therapeutic agent and electrical fields to a predetermined site within the skin and/or skeletal muscle of a patient in a manner that is effective, reproducible, and safe for both the operator and the patient. One embodiment of the apparatus comprises a single use subassembly "cartridge" and a hand-held "applicator". The single use sub-assembly integrates a reservoir for containing the agent of interest, at least one orifice through which the agent is delivered to the patient, and two or more electrodes capable of propagating electrical fields within the tissue. The hand-held applicator interfaces with the single use cartridge and incorporates automated mechanisms to (1) deploy the electrodes to the target tissue site, (2) position the orifice relative to the target tissue site, (3) transfer the agent from the reservoir through the orifice and into the target tissue site, and (4) relay electrical signals from a suitable pulse generator to the electrodes.

Although certain distinctions can be drawn between agents which are administered to patients for prophylactic purposes and agents which are administered for therapeutic purposes, in the context of the present invention such agents are considered to be substantially equivalent and will be referred to herein as therapeutic agents, unless otherwise indicated.

Apparatus Embodiments

The present invention provides an improved apparatus for safe, efficacious and reproducible, transcutaneous intramuscular (IM) delivery of therapeutic agents with Electrically Mediated Therapeutic Agent Delivery (EMTAD).

Figure 2:
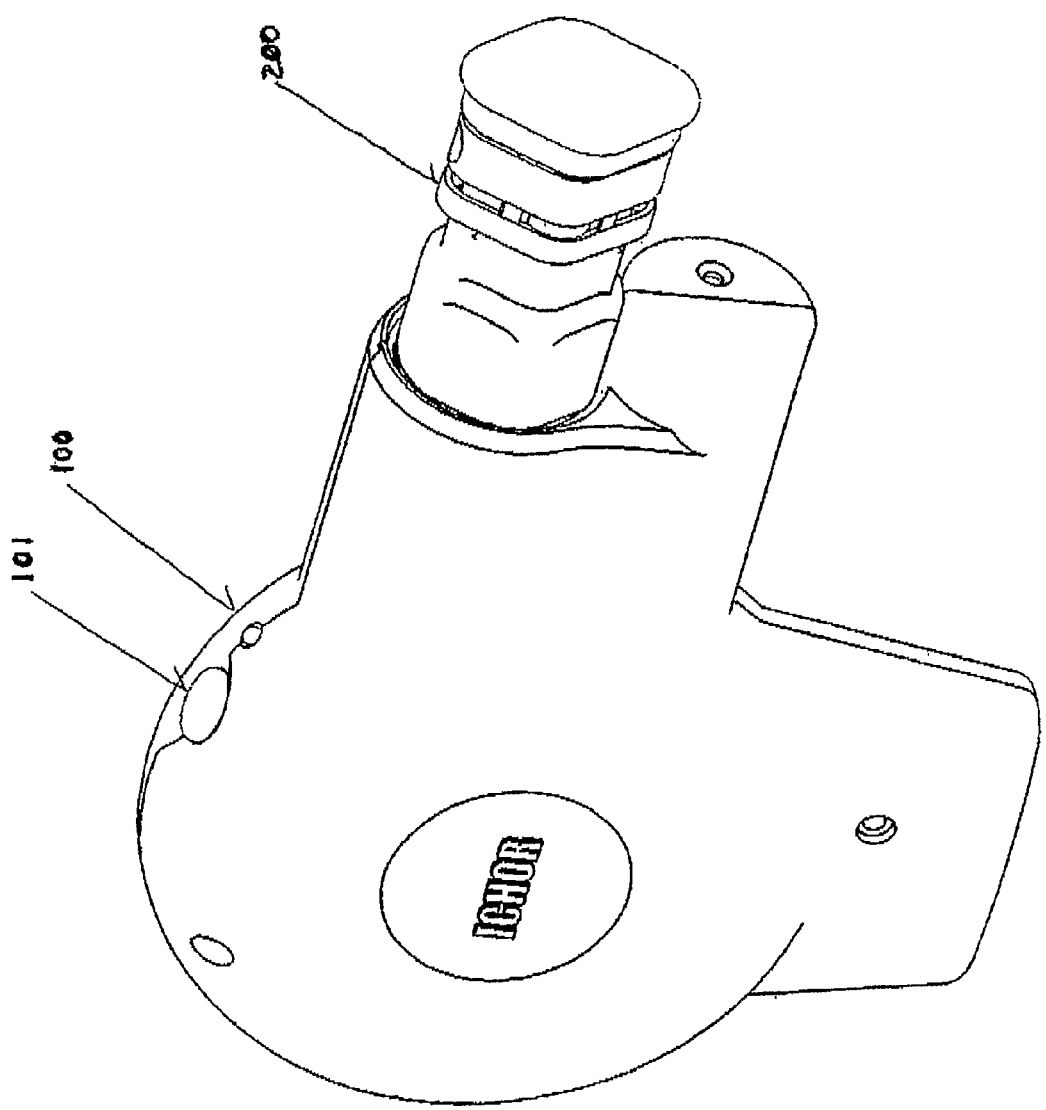
FIG. 2 illustrates the Cartridge of the embodiment of FIG. 1 assembled with the Applicator.
Figure 3:
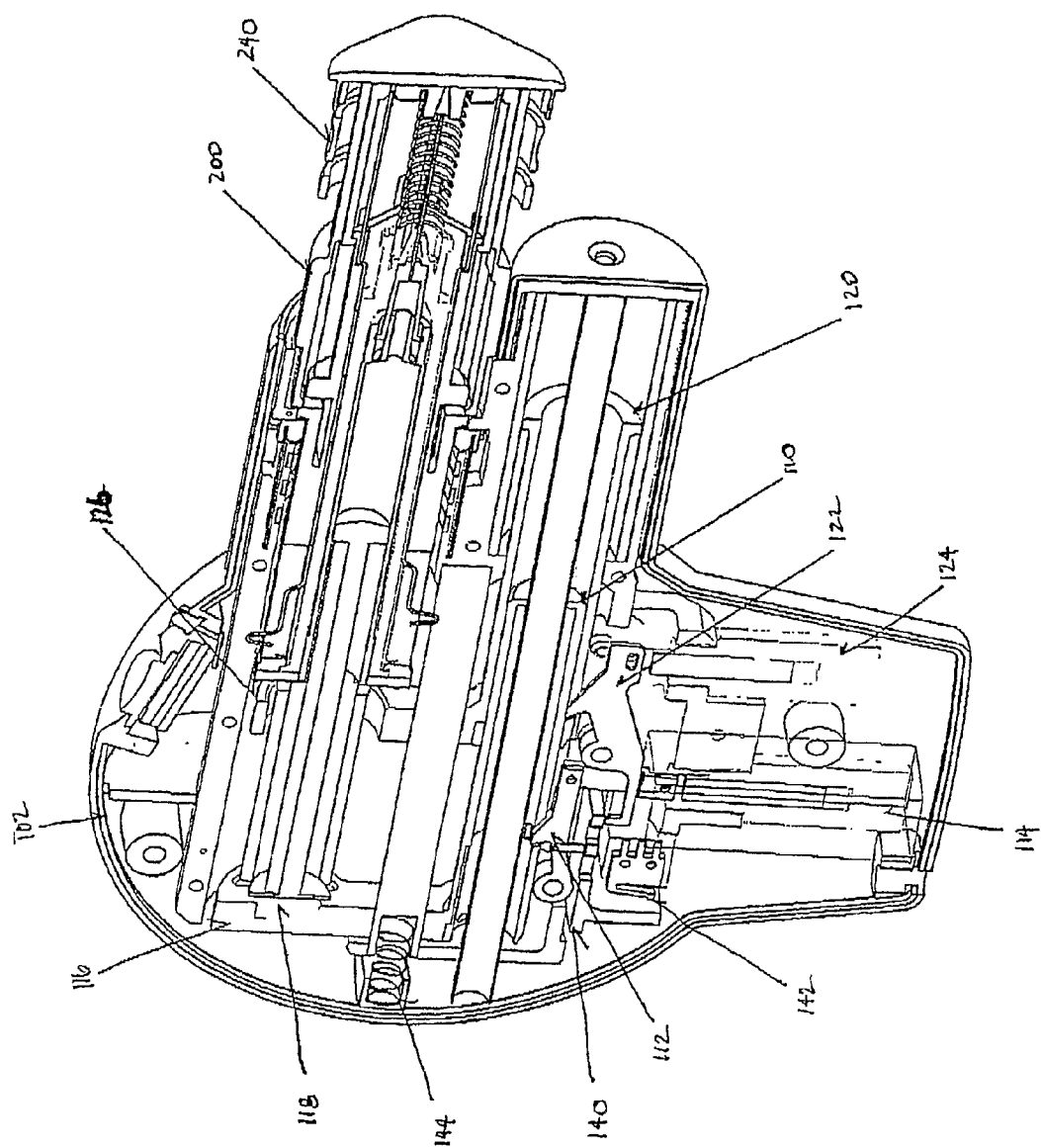
FIG. 3 is a cross sectional view of the Applicator/Cartridge/Syringe assembly of the embodiment of FIG. 1 with the insertion and injection spring mechanisms primed.
Figure 4:
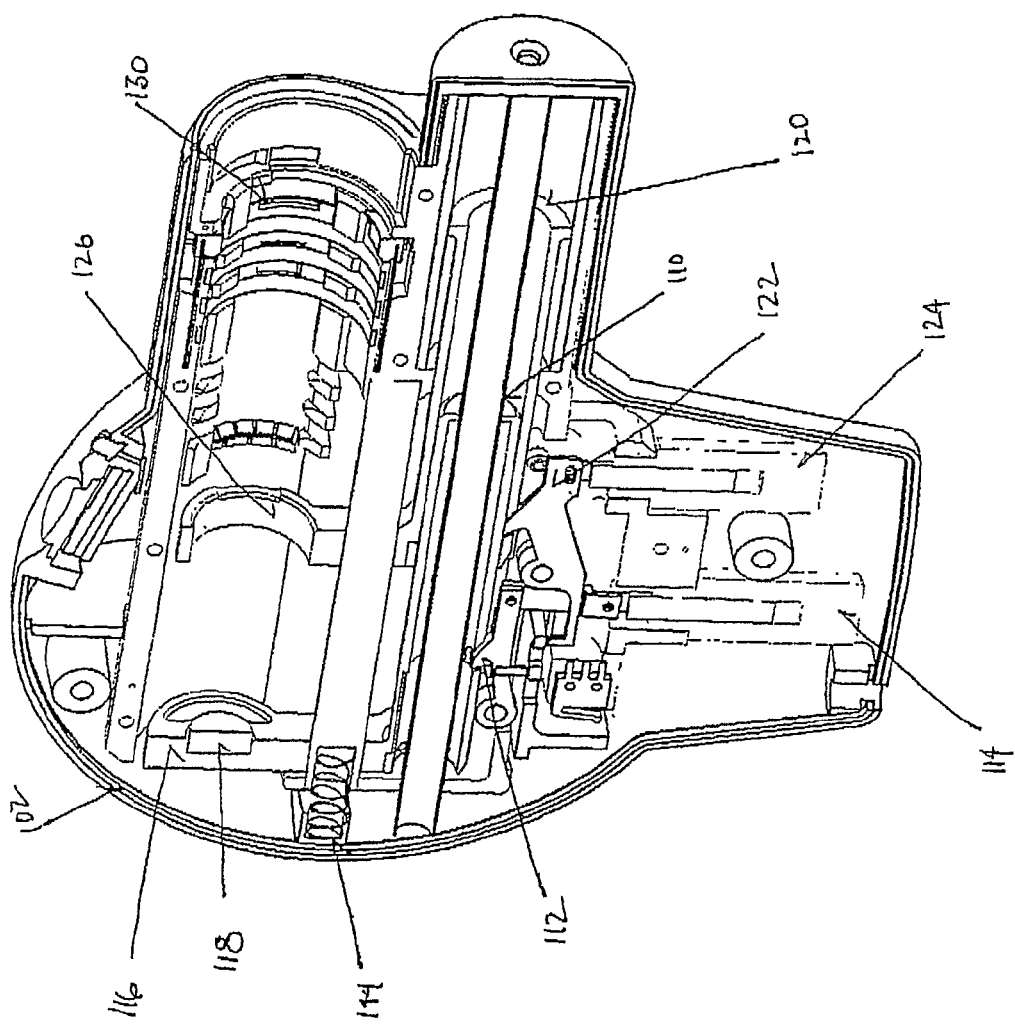
FIG. 4 is a cross sectional view of the Applicator of the embodiment of FIG. 1 with the insertion and injection spring mechanisms not primed.
Figure 5:
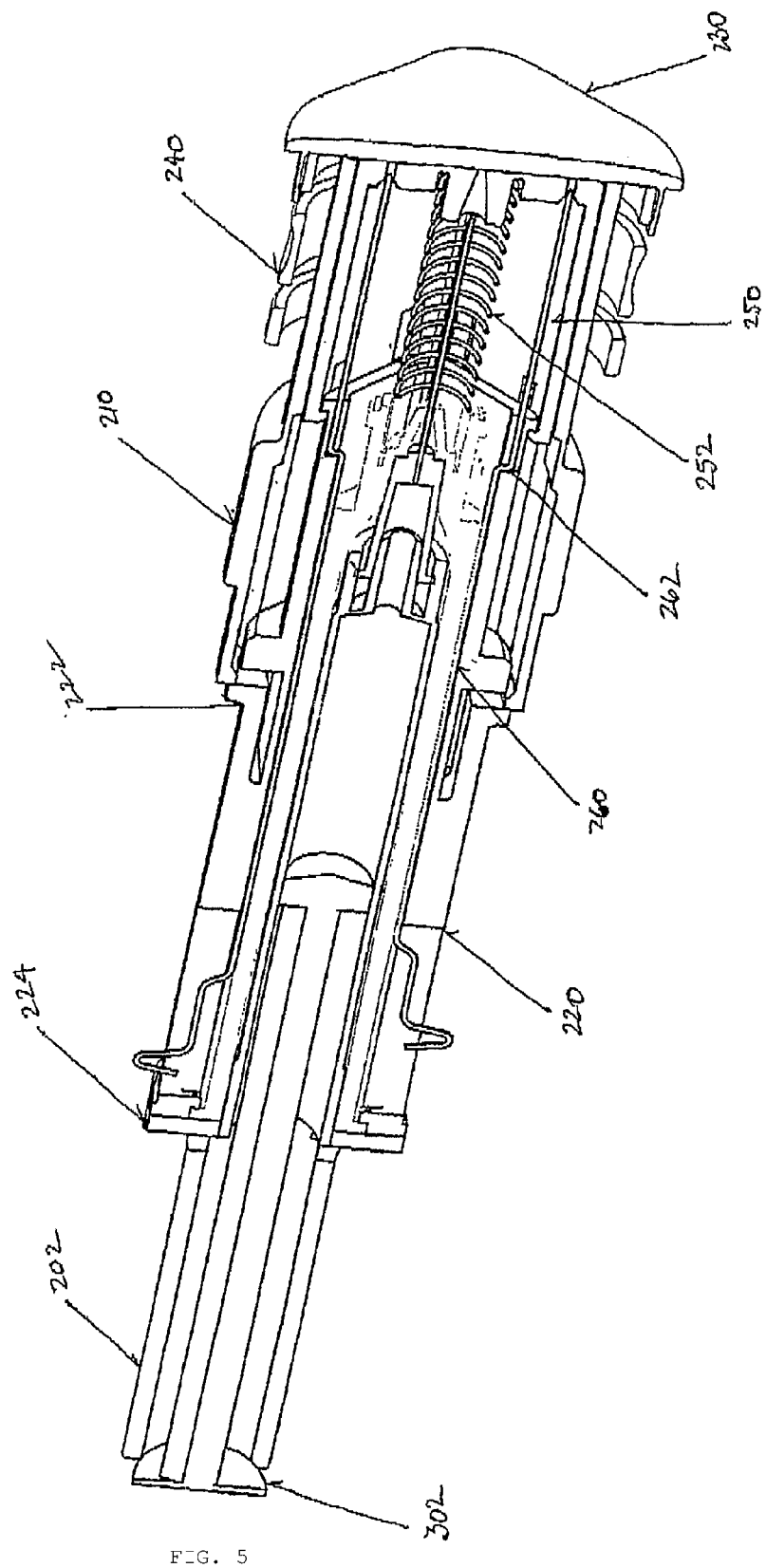
FIG. 5 is a cross sectional view of the Cartridge of the embodiment of FIG. 1 with the Syringe inserted.

A specific embodiment of an integrated unit for transcutaneous IM applications is illustrated in FIGS. 1-5. The apparatus consists of a main unit (applicator) 100 and a separable single use sub-assembly (cartridge) 200. The cartridge is configured to include a reservoir to contain the agent to be administered prior to delivery. The reservoir will be designed and constructed to maintain the agent in a stable environment and prevent contamination. The reservoir is operatively connected to an orifice through which the agent is administered into the patient. Most commonly, the reservoir and orifice are comprised of a syringe connected to a hollow injection needle 300. The cartridge encloses the electrode array and includes integral automatic protection against unwanted contact with the electrodes and/or the orifice/injection needle (i.e. "stick protection").

The applicator 100 incorporates a spring mechanism for automatic insertion of the electrode array and the injection needle into the target tissue. The applicator also includes a separate spring mechanism for automated controlled therapeutic agent injection through the incorporated syringe. The applicator incorporates a means to allow electrical communication with a suitable pulse generation device capable of controlling the treatment application sequence. Most commonly electrical communication is achieved through a conductive cable and connector. A trigger 101 on the applicator is utilized to initiate the treatment. Finally a system for identifying the inserted cartridge and setting the treatment parameters based on the cartridge is provided in the applicator.

Integration of Agent/Syringe with Cartridge

In previously disclosed devices of this nature, a means for administration of the therapeutic agent comprising a reservoir and at least one orifice through which the agent is administered have been described. In clinical practice of the previously disclosed invention it is desirable to integrate the means for administration of the therapeutic agent (reservoir and orifice) with the cartridge. Integrating the administration means with the cartridge can simplify the procedure by reducing apparatus handling. Reducing apparatus handling can also improve operator and patient safety by eliminating needle stick hazards and dosage errors. Integration also improves the accuracy of the predetermined spatial relationship between the agent delivery orifice and the electrode array.

There are several suitable embodiments of integrating the means of agent administration with the single use cartridge. The cartridge can be configured to accept a syringe and needle as the reservoir and orifice. It is desirable that once the syringe has been integrated with the cartridge that the integration is permanent. Permanent integration will prevent disassociation of the syringe and cartridge and reduce the possibility of needle stick injuries. The syringe can be an off-the-shelf syringe that is loaded with the agent prior to the agent administration procedure. Utilization of an off-the-shelf syringe allows one cartridge configuration to deliver numerous agent and dosage combinations. Additionally off-the-shelf syringes are readily available and cost effective. The syringe can alternatively be pre-filled with an agent and packaged with the cartridge. Utilization of a pre-filled syringe reduces the possibility for dosage errors. Additionally a pre-filled syringe does not require a plunger extending from the proximal end of the syringe to manually load the agent. Elimination of the plunger extension allows for a smaller apparatus that uses less material and is more ergonomic.

Another embodiment of integrating the reservoir and orifice with the cartridge is to incorporate the reservoir into the cartridge design thus eliminating the need for a separate syringe. It is preferable that the cartridge be constructed of an inert material to prevent reaction with the agent. Suitable materials include, but are not limited to, glass, polycarbonate and polyethylene.

It is desirable to store certain agents in a lyophilized state to improve shelf life. Such agents are mixed with a diluent prior to administration. A dual chamber reservoir where the lyophilized agent and the diluent are stored in the separate chambers can also be utilized for such agents. Prior to treatment the separation between the chambers is removed or broken to allow mixing of the agent and diluent. One suitable separation between the chambers is a stopcock valve that is manually opened. Another suitable separation is a thin film or a check valve that can be opened when adequate pressure is applied to the diluent chamber. Such a dual chamber reservoir can be incorporated into the cartridge.

A specific embodiment for integrating the means for agent administration with the cartridge is herein described. The specific embodiment utilizes an off-the-shelf syringe and needle 300 for the administration reservoir and orifice. The cartridge 200 is configured to accept the syringe and locate the needle orifice in a predetermined spatial relationship with the electrode array. Furthermore the cartridge is configured with snap tabs 224 that lock the syringe in place once it is inserted into the cartridge.

Drive Mechanisms

There are several mechanisms that are suitable as inanimate sources of energy to insert the electrodes and injection needle through the skin and into the targeted treatment tissue and also to inject the agent through the needle. A compressed gas powered mechanism is one such apparatus. Electro/mechanical mechanisms such as solenoids, linear motors and lead screws are also acceptable. However the preferred approach for transcutaneous electrode and injection needle insertion is the spring-based mechanism.

Electrode insertion mechanisms require sufficient force to rapidly penetrate the skin and implant the electrodes into the muscle. Rapid insertion can reduce tenting of the skin at the insertion site and thereby reduce deflection of the electrode or needle. Electrode deflection may distort the electrode array and effect treatment efficacy and patient safety. Needle distortion may effect co-localization of the agent and electrical fields. So it is desirable to insert the electrodes and needle rapidly to minimize deflection. Additionally rapid electrode/needle insertion reduces patient discomfort. The energy storage and discharge characteristics of spring-based mechanisms are well suited to enable rapid deployment of electrodes and injection needles into tissue with minimal distortion.

Insertion and injection mechanisms for transcutaneous applications also require sufficient linear motion (throw) to implant the electrodes to the target treatment depth and to inject the prescribed volume/dose of agent. Spring mechanisms are preferred since they can achieve adequate linear motion in a small and lightweight package. Additionally springs mechanisms do not require electrical or gas connections, they do not require consumables such as compressed gas canisters and finally they are cost effective.

Automatic/Passive Spring Priming

Although their functional characteristics and cost effectiveness make them preferable overall, spring mechanisms require priming. Energy is be imparted to and stored in the spring prior to actuating the treatment sequence. Previously disclosed devices of this nature require that the user actively perform a separate step to prime the spring mechanism prior to the use of the device. The disclosed invention includes means to automatically or passively prime the spring mechanism upon insertion of the cartridge 200 into the applicator 100. It is desirable that the priming of the spring mechanism ("spring priming") be accomplished in conjunction with the insertion of the cartridge 200 into the applicator 100. In addition to simplifying the procedure, automated/passive spring priming also eliminates the problematic failure mode of not priming the spring. A variety of energized mechanisms can be employed in the apparatus to accomplish automated spring priming. These mechanisms comprise an energy source, a suitable trigger, and a means to transfer energy from the energy source to the spring(s). Insertion of the cartridge into the applicator activates the trigger leading to the transfer of energy from the energy source to the spring(s). Sources of energy/mechanisms to achieve this function include but are not limited to compressed gas, solenoids and electrical motor-based mechanisms.

A preferred method and apparatus is to utilize the insertion and attachment of the cartridge 200 to the applicator 100 as a means to passively prime the spring mechanisms during cartridge insertion into the applicator—"cartridge priming". Utilizing the cartridge priming method provides the benefits of the described invention while eliminating the need for the additional priming mechanism required for automated spring priming. This simplifies the apparatus and reduces cost without sacrificing ease-of-use and safety.

In embodiments where the cartridge is utilized to prime spring drive mechanisms, there will be means to apply force to the injection drive mechanism through the cartridge without depressing the spring plunger and ejecting the agent from the syringe. Additionally, since the operator applies force to the cartridge to prime the spring mechanisms, it is desirable that the apparatus include means to prevent accidental deployment of electrodes and/or needles during the insertion of the cartridge into the applicator to prevent needle stick injuries. Moreover it is desirable that the means for stick prevention also prevent damage and/or contamination to the electrodes and needle during priming. Finally, in such an embodiment there is a risk that the operator may release the cartridge before completing priming. This may result in the stored spring energy ejecting the cartridge from the applicator causing injury and/or damage to the apparatus. Therefore it is desirable to prevent accidental ejection of the cartridge.

One specific embodiment is presented in FIGS. 1-5 for achieving the invention of cartridge priming. Those skilled in the art will appreciate that the specific mechanisms used to achieve car ridge priming are a matter of convenience and that the use of alternative mechanisms for achieving cartridge priming does not depart from the scope of the described invention. In the specific embodiment described herein, the cartridge 200 and applicator 100 are configured so that the cartridge 200 can only be inserted into the applicator 100 in a specific priming orientation. In the priming orientation, at least one cantilevered extension 202 of the cartridge engages the injection drive mechanism 110 and imparts the priming force to the mechanism while preventing the mechanism from contacting the syringe plunger 302. This specific embodiment provides stick prevention and protects the electrodes/needle from damage/contamination during priming by maintaining the electrodes/needle safely retracted and locked within the cartridge. Snap tabs 222 incorporated into the cartridge prevent the electrode hub 220 from moving axially relative to the cartridge collar 210 and thereby maintain the electrodes/needle safely retracted within the cartridge. Further stick and contamination protection is provided by a cap 230 over the distal end of the cartridge. The cap 230 is removed prior to treatment application. Preferably, the cap is constructed of puncture resistant material and the interface between the cap and the cartridge is designed to minimize the risk of contamination during handling. The electrode hub 220 engages the insertion drive mechanism 120 and transfers the priming force applied to the cartridge collar 210 to the insertion mechanism. To prevent accidental ejection of the cartridge during priming, this specific embodiment incorporates one-way leaf-spring latches 130 in the applicator that allow the cartridge to be inserted in the priming orientation but prevent it from being removed or ejected in that orientation. A ratchet mechanism is another suitable means to prevent accidental ejection of the cartridge. When the cartridge is completely inserted into the applicator, two spring-actuated latches 112, 122 capture the insertion and injection spring mechanisms and maintain them in their primed and energized state until they are actuated during treatment. A solenoid actuator 114, 124 is attached to each latch 112, 122 and when activated displaces the latch and releases the spring mechanism 110, 120.

Upon completion of the cartridge insertion and spring mechanism priming, the cartridge is twisted ¼ turn to complete attachment of the cartridge to the applicator. In this attached orientation the cantilevered extension 202 disengages from the injection drive mechanism 110 freeing the mechanism to act upon the syringe plunger 302 when the injection mechanism is released. Additionally in this attached orientation the applicator depresses the tabs 222 and frees the electrode hub to move axially relative to the cartridge, so the insertion mechanism can advance the electrodes and needle when the mechanism is released.

Designs Enabling Improved User Interface Factors

In the practice of the invention, ergonomics and human factors play a significant role in consistently providing safe and effective agent administration. The size and shape of the apparatus used for agent administration (the user interface) can affect the operator's ability to effectively deliver the agent to the target tissue site. It is desirable that the design of the apparatus facilitate accurate positioning of the apparatus in the proper location and orientation. Improper positioning of the apparatus can affect both the safety and efficacy of the treatment.

In addition to the human factors associated with the user, the size and shape of the device can also influence patient acceptance. A device can be threatening to patients, particularly if it is especially large, has a form suggestive of a weapon, or is otherwise intimidating. Therefore it is desirable that the device has a form factor that is both ergonomic and non-threatening. In previously disclosed devices of this nature, the drive mechanisms have been arranged co-linearly and in series with the cartridge. This results in a long and unwieldy device. The described invention utilizes one or more drive mechanisms arranged in parallel with the cartridge and the line of action of the electrodes and syringe. The parallel drive mechanisms can be arranged co-linearly or in an offset fashion. This parallel arrangement yields a more compact, ergonomic and non-threatening apparatus.

One specific embodiment employing offset parallel spring mechanisms is described in FIGS. 1-5, however, the invention can be adapted to achieve a desirable form factor utilizing other spring and drive mechanisms. For instance the spring may surround the electrode array or syringe.

Additionally the mechanism may utilize mechanical advantage to increase linear motion or force.

In the specific embodiment illustrated in FIGS. 1-5, the insertion and injection spring mechanisms are positioned within the applicator parallel and offset from the cartridge. The Force and motion of the spring mechanisms is transferred to the cartridge through drive arms 116, 126 that extend through the applicator and interface with the cartridge.

Cartridge Identification

In order to be well suited for use in clinical applications, an EMTAD device should accommodate the range of doses that may be prescribed for a given agent. When employing EMTAD, the "dose" of the agent is determined by the volume and concentration administered, the electrode array configuration and the electrical field parameters applied to the tissue (including waveform, voltage, duration, frequency, and number of pulses). In order to assure that the prescribed "dose" is applied to a given patient, the proper electrical parameters will be conveyed to the pulse generator. Although this can be accomplished through user input, such a system would carry a risk that a user error could result in a hazardous operating condition. Therefore it is desirable to provide an automated means for dosage recognition that minimizes the risk of a hazardous operating condition.

Although there are several automated means for dosage recognition a preferable method is accomplished in conjunction with the insertion of the cartridge into the applicator. In such an embodiment the electrical signal parameters partially determine dose are determined by the cartridge that includes the other two dose parameters (agent and electrode array). It is also desirable that the treatment sequence cannot be initiated until the electrical signal parameters are set. This assures safe and proper attachment of the cartridge to the applicator. In previously disclosed devices of this nature, programmable integrated circuits and other relatively expensive means have been described. In order to be well suited for commercial application the means for cartridge identification/electrical signal parameter recognition should be cost effective. In particular the components of the identification system and the associated manufacturing processes that are part of the single-use cartridge should be cost effective.

One skilled in the art will recognize that there are several suitable means for cartridge identification/electrical signal recognition. Suitable means include optical bar code identification and wireless radio frequency identification. In the case of bar code identification the bar code would be affixed or imprinted onto the cartridge and the reader would be integrated into the applicator. In the case of radio frequency identification the transponder would be integrated into the cartridge and the receiver would be included in the applicator. Preferably the receiver would be tuned only to receive the radio frequency signal when the cartridge was properly attached to the applicator. Another suitable method is to utilize a series of discrete switches in the applicator that may be closed when the cartridge is inserted. The pattern of open and closed switches would determine the electrical signal parameters. The switches could be electro/mechanical, opto/electro or any other suitable switch.

For example one embodiment utilizing three open contact pairs in the applicator 100 is illustrated. Conductive tape is affixed to the cartridge 200 to close the contact pairs when the cartridge is attached to the applicator. This 3-bit system will identify seven electrical signal parameter settings plus three open contact pairs will indicate when a cartridge is not attached. In addition to defining the administration dose, the described invention would also facilitate the use of a single application system for delivery of multiple classes of agents, which require different electrical conditions to achieve effective delivery.

Adjustable Treatment Depth

Efficacious, consistent, and safe application of EMTAD for intramuscular delivery relies in part on treating a consistent volume of muscle tissue. However, there is a significant variation between patients and treatment sites in the subcutaneous fat pad thickness that is penetrated to access the targeted muscle tissue. In one study, (Poland G A, et al. *JAMA*. 1997 Jun. 4; 277(21):1709-11) a range of deltoid fat pad thickness from 3.7 mm to 35.6 mm is reported. So for a given electrode array size, the volume of muscle tissue affected will vary depending on the fat pad thickness. Additionally the thickness of tissue between the skin and the bone also vary significantly between patients and between treatment sites. So an electrode/needle length appropriate to treat a large patient may impact bone during insertion into a small patient. Electrode contact with bone could cause injury to the patient and/or it could distort the electrode array and effect safety and efficacy of the treatment. It is therefore desirable to provide a means for adjusting the depth of electrode/needle penetration based on the treatment site and patient anatomy.

In the present invention, an adjustable ring 240 over the distal tip of the present invention modifies the electrode/needle penetration depth. The ring can be adjusted axially relative to the cartridge 200 tip so that the length of the ring that extends beyond the distal tip of the apparatus reduces the length of electrode/needle that penetrate into the patient. The specific embodiment illustrated in FIGS. 1-5 utilizes a diamond shaped ring that snaps into discrete axial positions. To modify its position, the major axis of the diamond shaped ring is compressed causing the minor axis to expand and release the ring from the cartridge. Another suitable embodiment is a ring that is threaded onto the cartridge tip and can be adjusted by threading the ring back and forth on the cartridge. This embodiment allows for a continuous number of depth adjustment positions.

Automatic/Passive Release of Trigger Safety

Inadvertent release of the primed insertion and injection spring mechanisms can result in injury, loss of therapeutic agent and/or damage to the device. It is therefore desirable to provide a safety system to prevent accidental release of the spring mechanisms. It is preferable that such a safety system prevent accidental release of the spring mechanisms due to external forces such vibration and impact. Additionally, the operator may inadvertently activate the treatment sequence when handling the device, so it is also preferable that the safety system prevent activation of the treatment sequence unless the device is properly applied to the treatment site. Proper placement at the treatment site can also affect treatment efficacy. For instance, the device is desirably applied to the treatment site with adequate force to assure that the electrodes/needle penetrate into the tissue to the full-prescribed depth. Preferably the safety system is automatically and passively deactivated when the device is applied to the treatment site with adequate force. Automatic and passive disablement of the safety system does not require a separate operator step. In addition to simplifying the procedure, automated/passive safety disablement also eliminates the possible failure mode of not deactivating the safety system.

To ensure that the electrodes/needle penetrate into the tissue to the full-prescribed depth, the minimum force with which the device is applied to the treatment site (the "application force") will exceed the force necessary to insert the electrodes/needle (the "electrode insertion force"). The electrode insertion force is dependent upon several variables, which are disclosed in detail herein below. By way of example, a typical electrode insertion force may be 2.5 pounds (11.1 Newtons), therefore, the minimum application force would be 2.5 pounds (11.1 Newtons). Preferably, a margin of safety would be added to the insertion force so the application force would be between 3.5 and 5.0 pounds (15.6-22.2 Newtons). Preferably the required application force will not exceed a force that the operator can comfortably apply to the treatment site.

A preferred embodiment of the disclosed safety system is herein described. Within the applicator 100 at least one mechanical stop 140 physically prevents the latches 112, 122 from disengaging from the insertion 120 and injection 110 spring mechanisms. The connection between the applicator trigger and the pulse generator is maintained open by an electronic switch 142 thereby preventing accidental activation of the treatment sequence. The internal mechanisms of the applicator float axially within an outer housing 102 and are maintained in an extended position by a spring 144 acting between the internal applicator and the external housing. The spring is equal to the preferred application force. When the apparatus is applied to the treatment site with adequate pressure to overcome the spring force, the internal applicator is repositioned within the outer housing 102. In this position the safety systems are disabled. The stop 140 is repositioned relative to the latches and no longer prevents the latches from disengaging from the insertion and injection spring mechanisms. Furthermore the electronic switch 142 contacts the outer housing and is closed allowing the trigger to communicate with the pulse generator and initiate the treatment sequence.

Electrode Array Insertion Spring Force/Rate

Electrode insertion mechanisms require sufficient force to rapidly penetrate the skin and implant the electrodes into the muscle. Rapid insertion can reduce tenting of the skin at the insertion site and thereby reduce deflection of the electrode or needle. Electrode deflection may distort the electrode array and effect treatment efficacy and patient safety. Needle distortion may effect co-localization of the agent and electrical fields. So it is desirable to insert the electrodes and needle rapidly to minimize deflection. Additionally rapid electrode/needle insertion reduces patient discomfort. The energy storage and discharge characteristics of spring-based mechanisms are well suited to enable rapid deployment of electrodes and injection needles into tissue with minimal distortion.

Several variables influence the spring force necessary for rapid intramuscular electrode insertion including electrode diameter, number of electrodes, spacing between electrodes and electrode tip geometry. For intramuscular EMTAD, common electrode diameters range from 0.25 mm to 1.50 mm and typical electrode array configurations contain from 2 to 7 electrodes. The force required to insert the electrode arrays within these ranges is proportional to both the electrode diameter and to the number of electrodes. For instance increasing the electrode diameter and/or increasing the number of electrodes results in an increase of the minimum required insertion force. Electrode spacing on the other hand is inversely proportional to the spacing between electrodes. Due to the interaction of tissue that is displaced as the electrode is inserted smaller electrode spacing result in higher insertion force. Typical EMTAD apparatus, incorporating arrays of penetrating electrodes utilize an intra-electrode spacing at least 10 times greater than the diameter of the electrodes comprising the array and more commonly 15-20 times greater. Within this range there is little interaction of displaced tissue and therefore electrode spacing has minimal effect on the insertion force. Cutting electrode tip geometry is preferred to minimize insertion force. Blunt and dilating tip geometry requires increased insertion force.

Experiments are carried out to determine minimum spring force/rate necessary for rapid percutaneous intramuscular electrode implantation. A selection of electrode arrays appropriate for intramuscular application of EMTAD and with cutting tip electrodes is evaluated. Each electrode array is implanted into a porcine model and the minimum spring force necessary to rapidly penetrate the cutaneous tissue and implant the electrode array without significant distortion is determined. Because of the force exerted by a spring decreases as the energy is released from the spring two results are given. The first is the force at the beginning of the spring stroke and represents the minimum force necessary to penetrate the cutaneous tissue. The second is the force at the end of the spring stroke and represents the minimum force necessary to implant the electrode array through the sub cutaneous and muscle tissue. Because the forces are dependent upon the electrode diameter and the number of electrodes the results are given as a ratio of force to total cross-sectional area of the electrodes in the array. The results indicate that a minimum of 1000 pounds of force per square inch (0.7 kilograms per square millimeter) of cross-sectional area of electrodes at the beginning of the implant stroke and a minimum of 500 pounds of force per square inch (0.35 kilograms per square millimeter) of cross-sectional area of electrodes at the end of the implant stroke is desirable to implant the electrodes. In order to assure consistent and reliable deployment of the electrodes an initial implant force of at least 2000 pounds per square inch (1.4 kilograms per square millimeter) of electrode cross sectional area and a terminal implant force of at least 750 pounds of force per square inch (0.5 kilograms per square millimeter) of cross-sectional area of electrodes is preferred.

By way of example, an array comprised of 4 electrodes, each with a diameter of 0.02 inches would have a total cross-sectional area of approximately 0.00125 square inches (0.8 square millimeters). Thus a mechanism for deployment of the example array would require a minimum force of 1.25 pounds (5.5 Newtons) to achieve insertion and more preferably a force of at least 2.50 pounds (11 Newtons).

In embodiments where the spring mechanisms are manually primed, it is preferable to limit the force of the springs so that the operator can comfortably prime the springs. A preferred limit for spring priming is less than 15 pounds force (67 Newtons). For embodiments where each spring mechanism is primed separately the maximum force for a spring is 15 pounds (67 Newtons). However for those embodiments where the insertion and injection spring mechanisms are primed simultaneously the combined spring force preferably will not exceed 15 pounds (67 Newtons).

Agent Administration Spring Force/Rate

Several variables affect the force necessary to administer the therapeutic agent. These variables include, agent viscosity, cross-sectional area of the syringe, needle gauge, cross-sectional area of orifice(s), and tissue density. For parameters typical of intramuscular EMTAD the minimum spring force necessary to administer the therapeutic agent is 0.25 pounds (1.1 Newtons). Preferably the injection spring force is between 1 and 10 pounds (4.5-45 Newtons).

Although the functional characteristics and cost effectiveness of the injection spring mechanism makes it preferable overall, the impact of the drive mechanism onto the syringe plunger can create a "water hammer" effect. The force wave generated from the impact can travel through the agent within the syringe and result in damage to the syringe or needle. In particular, standard plastic needle hubs may crack or split causing the agent to leak before it is completely administered. It is therefore desirable to damp the impact energy of the drive mechanism without affecting the force/rate of agent injection.

There are several means to damp the impact energy of the drive mechanism. One such means is to position an energy absorbing material 118 between the syringe plunger 302 and drive mechanism 116. Appropriate energy absorbing materials include but are not limited to elastomers such as silicone and polyurethane and closed-cell foams. Another suitable means to absorb the impact is gas/fluid dampening to slow the rate of the drive mechanism. Such an apparatus requires that at least a portion of the injection drive mechanism displace a gas or fluid through a small bleed hole in order to move forward. Preferably the gas is air and the bleed hole is tuned so that the dampening or is less than the dampening produced from administering the agent through the injection needle. In such a case, the gas dampening will only affect the rate of the drive mechanism until it contacts the syringe at which point the dampening produced from administering the agent through the injection needle will be the limiting factor affecting agent administration.

Automatic/Passive Stick Prevention

Post treatment the electrodes and injection needle present a hazard for needle sticks and transfer of blood borne pathogens. Therefore it is desirable that the apparatus includes integral stick protection. Moreover it is desirable that the stick protection is both automatic and passive. Automatic stick protection will eliminate possible injury when manually deploying the stick protection and it also eliminates the possible failure mode of not deploying the stick protection. Preferably, upon activation the stick protection includes a means for locking in place to prevent possible someone from defeating the stick protection once it has deployed.

One preferred embodiment of an integral automatic locking stick protection is presented. However one skilled in the art will appreciate that other embodiments that can achieve the same objective. The specific embodiment herein described utilizes a stick shield 250 integral to the cartridge that automatically extends over the electrodes/needle as they are removed from the patient. A compression spring 252 within the cartridge is positioned proximal to the stick shield between the stick shield and the electrode hub 220. As the electrode hub advances distally during electrode/needle insertion the spring is compressed. When the electrodes/needle are removed post treatment from the patient, the spring extends and extends the stick shield distally over the electrodes and needle. As the shield is completely extended over the electrodes and needle cantilevered tabs on the stick shield snap into corresponding grooves in the collar 210 thereby locking the shield in the extended position.

Single Use

Users may attempt to reuse the single use cartridge to save costs or to apply an off label agent. Reusing the cartridge may affect the safety and efficacy of the treatment. For instance coatings on the electrodes that may be utilized to assure biocompatibility may not withstand multiple uses so the treatment may produce a toxic result in the patient. Additionally, sterility of a reused device cannot be assured. It is therefore desirable to include features in the apparatus that prevent reuse.

The apparatus herein described includes three features that prevent reuse. The stick shield 250 locks in an extended position preventing the electrodes and needle from being inserted into the patient. The syringe is permanently attached to the cartridge when it is inserted, so the syringe cannot be detached to reload it with the agent. Finally, after electrode insertion the cartridge hub/collar configuration is fixed with the hub inserted into the collar. In this configuration the cartridge will not prime the insertion and injection spring mechanisms. Also in this configuration the cartridge identification contacts in the applicator will not communicate with the cartridge so the control system will not recognize the cartridge and will prevent treatment.

Those skilled in the art will recognize that there are other suitable means for preventing reuse. One such method is to incorporate a fuse into the cartridge and apply a signal from the pulse generator that blows the fuse at the end of the treatment. Another such means is to identify each cartridge with a unique serial number that is read by the applicator. The pulse generator would store the serial numbers and not apply treatments through cartridges whose serial numbers have already been read and stored.

Manufacturability

In order to be well suited for commercial application, the manufacturing costs of a single-use cartridge should be as low as possible. In addition, when applying EMTAD multiple electrode array configurations may be required to deliver a range of doses prescribed for a given agent. One method of reducing manufacturing costs while producing multiple array configurations is to utilize many of the same components in the multiple cartridge configurations. This approach will reduce costs including but not limited to tooling costs, inventory costs, quality control costs and handling costs.

In the specific embodiment illustrated in FIG. 5, the electrode array configuration is modified by changing the geometry of only the electrodes 260. A bend 262 near the distal end of the electrode changes the relative position of the penetrating end of the electrodes within the cartridge and thus changes the array configuration. The cartridge components are designed to accept multiple electrode geometries and therefore can be utilized in multiple electrode array configurations. Additionally the cartridge components have been designed to snap together and utilize the bend in the electrode to securely capture the electrodes between the cartridge components. This approach further reduces fabrication costs by elimination more costly joining techniques such as adhesive joints, solvent bonding, insert molding and ultrasonic welding.

All patents and patent applications cited in this specification are hereby incorporated by reference as if they had been specifically and individually indicated to be incorporated by reference.

Although the foregoing invention has been described in some detail by way of illustration and Example for purposes of clarity and understanding, it will be apparent to those of ordinary skill in the art in light of the disclosure that certain changes and modifications may be made thereto without departing from the spirit or scope of the appended claims.

What is claimed is:

1. A method comprising:

administering a therapeutic agent to a predetermined site within the tissue of a patient by:

loading the therapeutic agent into an apparatus comprising:

a) a plurality of penetrating electrodes arranged in a predetermined spatial relationship, each electrode with a cross sectional area contributing to a total cross sectional area of all electrodes;
b) an applicator housing an inanimate source of energy operatively connected to said plurality of electrodes, and wherein said source of energy is configured to provide a force sufficient to rapidly insert the electrodes; and
c) an electrical field generator operatively connected to said electrodes at least in their deployed state; and
d) at least one cantilevered extension of a cartridge that engages an injection drive mechanism of said applicator to passively prime said inanimate source of energy when said cartridge is inserted into said applicator;
positioning the apparatus against the patient;
deploying the electrodes using the source of energy;
generating an electric field between the electrodes at the predetermined site; and
delivering the therapeutic agent to the predetermined site;
wherein the administering does not result in tenting of the skin of the patient or significant distortion of the electrodes.

2. The method of claim 1, wherein the apparatus is configured to accept a fluid reservoir for containing the therapeutic agent said reservoir operatively connected to at least one injection orifice.

3. The method of claim 2 wherein the reservoir and orifice comprise a needle and syringe.

4. The method of claim 3 wherein the syringe is provided pre-filled with the therapeutic agent.

5. The method of claim 2 wherein the reservoir comprises a glass vial.

6. The method of claim 2 wherein the reservoir and orifice comprise a subassembly that can be separated from the source of energy.

7. The method of claim 2 wherein the electrodes, reservoir, and orifice are housed within a single subassembly that can be separated from the source of energy.

8. The method of claim 7 wherein the reservoir is provided pre-filled with the therapeutic agent.

9. The method of claim 2, wherein the fluid reservoir comprises a dual chamber reservoir.

10. The method of claim 9, further comprising resuspending a lyophilized therapeutic agent in the dual chamber reservoir prior to the delivering of said therapeutic agent.

11. The method of claim 1 wherein the source of energy to deploy the electrodes is at least one spring.

12. The method of claim 1 wherein the source of energy to deploy the electrodes is at least one compressed gas.

13. The method of claim 1 wherein the source of energy to deploy the electrodes is a linear motor.

14. The method of claim 1 wherein the electrodes comprise a subassembly that can be separated from the source of energy.

15. The method of claim 1 wherein the electrodes comprise a conductive metal coated with a conductive, electrochemically stable compound.

16. The method of claim 15 wherein said conductive, electrochemically stable compound is selected from the group consisting of: titanium nitride, platinum, platinum iridium alloys, and iridium oxide.

17. The method of claim 1 wherein the electrical field generator is configured to induce an electrical field of from approximately 50 to approximately 300 V/cm between at least two of said electrodes.

18. The method of claim 1 wherein the electrical field generator is configured to generate said electric field for a duration of from approximately 1 microsecond to approximately 100 milliseconds and at a frequency of from approximately 0.1 Hertz to approximately 1 megahertz between at least two of said electrodes.

19. The method of claim 1, wherein the apparatus is a single use apparatus.

20. The method of claim 1, wherein said apparatus is configured to provide an initial implant force of at least 2000 pounds per square inch (1.4 kilograms per square millimeter) of the total cross sectional area of all electrodes and a terminal implant force of at least 750 pounds of force per square inch (0.5 kilograms per square millimeter) of the total cross sectional area of all electrodes.

21. The method of claim 1, wherein the force provided by the source of energy is at least 1000 pounds per square inch (0.7 kg/square millimeter) of the total cross sectional area of all electrodes.

* * * * *